US011519084B2

(12) United States Patent
Kumar et al.

(10) Patent No.: US 11,519,084 B2
(45) Date of Patent: Dec. 6, 2022

(54) MEMBRANE-LESS REACTOR DESIGN AND PROCESS FOR BIOTRANSFORMATION OF CARBON DIOXIDE

(71) Applicants: Indian Oil Corporation Limited, Mumbai (IN); Vlaamse Instelling voor Technologisch Onderzoek NV (VITO), Mol (BE)

(72) Inventors: Manoj Kumar, Haryana (IN); Srikanth Sandipam, Haryana (IN); Suresh Kumar Puri, Haryana (IN); Sankara Sri Venkata Ramakumar, Haryana (IN); Ludovicus Diels, Mol (BE); Lambertus Bouwman, Mol (BE); Karolien Vanbroekhoven, Mol (BE); Deepak Pant, Mol (BE)

(73) Assignees: Indian Oil Corporation Limited, Mumbai (IN); Vlaamse Instelling voor Technologisch Onderzoek NV (VITO)

( * ) Notice: Subject to any disclaimer, the term of this patent is extended or adjusted under 35 U.S.C. 154(b) by 0 days.

(21) Appl. No.: 17/084,623

(22) Filed: Oct. 29, 2020

(65) Prior Publication Data
US 2021/0170357 A1 Jun. 10, 2021

(30) Foreign Application Priority Data
Dec. 4, 2019 (IN) .............................. 201911050001

(51) Int. Cl.
*C25B 9/07* (2021.01)
*C25B 11/073* (2021.01)
(Continued)

(52) U.S. Cl.
CPC ................. *C25B 9/07* (2021.01); *C25B 3/07* (2021.01); *C25B 3/26* (2021.01); *C25B 9/01* (2021.01);
(Continued)

(58) Field of Classification Search
CPC ......... C25B 9/01; C25B 9/015; C25B 11/031; C25B 11/032
See application file for complete search history.

(56) References Cited

U.S. PATENT DOCUMENTS 7,709,113 B2 * 5/2010 Logan ..................... H01M 8/16
204/266
2008/0277273 A1 * 11/2008 Logan ..................... C02F 3/005
204/267
(Continued)

FOREIGN PATENT DOCUMENTS

CN 104628133 A * 5/2015 .............. C02F 3/301
CN 105776502 A 7/2016
(Continued)

OTHER PUBLICATIONS

Srikanth et al, Electro-biocatalytic conversion of carbon dioxide to alcohols using gas diffusion electrode, Bioresource Technology, vol. 265, Oct. 2018, pp. 45-51 (Year: 2018).*
(Continued)

*Primary Examiner* — Harry D Wilkins, III
(74) *Attorney, Agent, or Firm* — Blank Rome LLP (57) ABSTRACT

The present invention discloses a membrane-less reactor design for microbial electrosynthesis of alcohols from carbon dioxide ($CO_2$). The membrane-less reactor design thus facilitates higher and efficient $CO_2$ transformation to alcohols via single pot microbial electrosynthesis. The reactor design operates efficiently avoiding oxygen contact at working electrode without using membrane, in turn there is an increase in $CO_2$ solubility and its bioavailability for subsequent $CO_2$ conversion to alcohols at faster rate. The present invention further provides a process of operation of the reactor for biotransformation of the carbon dioxide.

8 Claims, 2 Drawing Sheets

(51) Int. Cl.
  *C25B 9/01* (2021.01)
  *C25B 3/07* (2021.01)
  *C25B 15/08* (2006.01)
  *C25B 11/032* (2021.01)
  *C25B 3/26* (2021.01)
  *C25B 15/02* (2021.01)

(52) U.S. Cl.
  CPC .......... *C25B 11/032* (2021.01); *C25B 11/073* (2021.01); *C25B 15/02* (2013.01); *C25B 15/085* (2021.01); *C25B 15/087* (2021.01)

(56) References Cited

U.S. PATENT DOCUMENTS

| | | | | |
|---|---|---|---|---|
| 2011/0311887 | A1* | 12/2011 | He | C02F 3/005 210/601 |
| 2012/0132521 | A1* | 5/2012 | Silver | C25B 3/00 204/252 |
| 2012/0199492 | A1 | 8/2012 | Jin et al. | |
| 2012/0288898 | A1* | 11/2012 | Lovley | C12P 7/16 435/140 |
| 2013/0256149 | A1* | 10/2013 | Popat | C25B 1/04 204/260 |

FOREIGN PATENT DOCUMENTS

| | | | | |
|---|---|---|---|---|
| RU | 2199799 C | * | 2/2003 | ............ H01M 4/86 |
| WO | WO 2013/066331 A2 | * | 5/2013 | ............ C25B 1/04 |
| WO | WO-2015/035521 A1 | | 3/2015 | |

OTHER PUBLICATIONS

Christodoulou et al., The use of carbon dioxide in microbial electrosynthesis: Advancements, sustainability and economic feasibility, Journal of CO2 Utilization, vol. 18, Mar. 2017, pp. 390-399 (Year: 2017).*

Call et al, Hydrogen Production in a Single Chamber Microbial Electrolysis Cell Lacking a Membrane, Environmental Science & Technology, vol. 42, No. 9, Mar. 2008, pp. 3401-3406 (Year: 2008).*

"Gas Diffusion Electrodes", Vito NV, accessed on Apr. 22, 2022 at https://vito.be/en/product/gas-diffusion-electrodes (Year: 2022).*

C. G. S. Giddings, et al., "Simplifying Microbial Electrosynthesis Reactor Design", Frontiers in Microbiology, Original Research, May 15, 2015, 6 pgs.

S. Bajracharya, et al., "Application of Gas Diffusion Biocathode in Microbial Electrosynthesis from Carbon Dioxide", Environ Sci Pollut Res, Nov. 2015, 17 pgs.

* cited by examiner

Figure 1: Schematic representation of reactor design

Figure 2: Process flow diagram of reactor operation

MEMBRANE-LESS REACTOR DESIGN AND PROCESS FOR BIOTRANSFORMATION OF CARBON DIOXIDE

RELATED APPLICATION

This application claims the benefit of Indian Application No. 201911050001, filed on Dec. 4, 2019. The entire disclosure of this application is hereby incorporated by reference.

FIELD OF THE INVENTION

The present invention relates to a membrane-less reactor design for microbial electrosynthesis of alcohols from carbon dioxide ($CO_2$). The novel system has no membrane, which is one of the limitations for up scaling these systems, and is also equipped with bio-electro-active filter for faster and efficient $CO_2$ conversion. Such reactor design would be suitable to get selective product synthesis that makes the downstream processing easy.

BACKGROUND OF THE INVENTION

Microbial electrosynthesis (MES) is a process of converting $CO_2$ to value-added products like fuels such as alcohols and chemicals through electrode-assisted microbial process. Though, the proof of concept was established in 2010 and several studies reported the product synthesis from $CO_2$ using different bacteria, the process has not yet further moved from lab-scale due to some inherent limitations, such as requirement of membrane in reactor design, mass transfer limitations caused by the limited $CO_2$ solubility & bioavailability, synthesis of mixture of products, slow reaction rates, etc. Hence, there is an urgent need to develop reactor design that can address all these issues and can deliver selective product at the end.

Few studies are available in literature which attempts to address one or more of these issues. However, they do not completely address all the above mentioned pertinent issues.

US20120199492 of Next Fuel Inc., discloses a bioelectrochemical conversion and sequestration of carbon dioxide into organic compounds, discloses a simple dual chambered bioelectrochemical system for conversion of $CO_2$ to value added products. The invention relates to microbial electrosynthesis at cathode and its operating conditions for conversion of $CO_2$. This invention does address the shortcomings discussed above.

WO2015035521A1 of Mantra Energy Alternatives Ltd discloses a membrane-less electrochemical reactor for electro-reduction of $CO_2$ to products such as methanol and other organic compounds of low molecular mass. The reactor may have single or multiple electrochemical cells, where the anode has an electro-catalytic surface selected from titanium and the 3D cathode comprises an electronically conductive gas diffusion cathode layer. Also, the feed gas may contain about 1 to 100 volume % $CO_2$. However, the process is focused on electro-chemical reduction.

CN105776502B of Zhejiang Technology and Business University discloses a metal oxide modified electrode biomembranes to restore $CO_2$ using a three-electrode system. In the three-electrode system, a precursor solution of $Fe^{2+}$ or $Cu^{2+}$ is used as an electrolyte, a conductive substrate is used as a working electrode, a titanium electrode is a counter electrode, and an Ag/AgCl electrode is used as a reference electrode. This is however based on the use of biomembranes.

CG Giddings et al., 2015 discloses microbial electrosynthesis to efficiently convert $CO_2$ into organic commodities. The purpose of the study described here was to determine if microbial electrosynthesis reactors could be simplified by removing potentiostat control of the cathode and reconfiguring the anode and cathode to make it possible to avoid a separator membrane. It however, does not disclose the use of gas diffusion electrode.

Bajracharya et al., 2016 discloses application of gas diffusion biocathode in microbial electrosynthesis from $CO_2$, is a research article (from some of the inventors of this application) based on application of gas diffusion electrode (GDE) for $CO_2$ conversion. They used the GDE in a membrane based reactor and studied the conversion of $CO_2$ to products. Major limitation of this study is detachment of biofilm from the active layer of GDE and also, they produce only acetic acid as major product.

Srikanth et al., 2018 provides an electro-biocatalytic conversion of $CO_2$ to alcohols using gas diffusion electrode, is a similar study, where the authors used selectively enriched mixed culture for the $CO_2$ conversion to alcohols. This is also based on membrane based reactor study using $CO_2$ as carbon source. Major limitation of the study is also biofilm detachment and product selectivity.

SUMMARY OF THE INVENTION

Microbial electrosynthesis is a promising strategy for the production of fuels and other organic commodities from $CO_2$ with higher efficiencies. A major challenge, however, is the design of a robust reactor. It is known in the art that the membranes in reactors add substantial cost and designing large scale reactors with two chambers separated by a membrane is challenging. Hence, a membrane-less reactor design is highly desirable.

Objectives of the Invention

It is the main objective of the present invention to provide a membrane-less reactor for conversion of $CO_2$ to alcohols by single pot microbial electrosynthesis.

Further the object of this invention is providing a gas diffusion electrode as a working electrode with an active layer modified with an electroactive material.

Further the object of the invention is to provide a two-stage conversion of carbon dioxide to alcohols via organic acids in single pot with the gas diffusion electrode and a bio-electroactive filter arrangement.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps of the process, features of the product, referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products and methods are clearly within the scope of the disclosure, as described herein.

The present invention provides a membrane-less reactor design for higher and efficient $CO_2$ transformation to alcohols via single pot microbial electrosynthesis. This reactor design avoids the oxygen contact at working electrode without using membrane, also increases the $CO_2$ solubility and its bioavailability for the $CO_2$ conversion to alcohols at faster rate.

Figure 1:
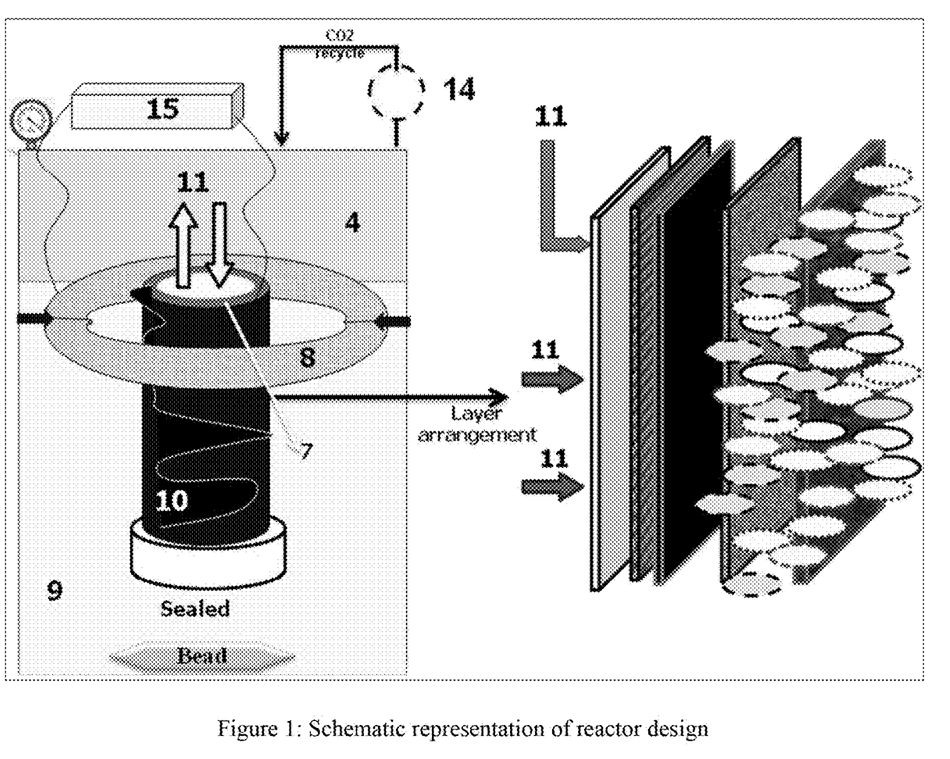
FIG. 1: Schematic representation of reactor design.

In an embodiment of the invention, the membrane-less reactor comprises a tubular gas diffusion electrode (GDE) with an active layer modified with an electroactive membrane as a working electrode, a circular counter electrode, a porous bio-electroactive filter, an electrolyte and sampling ports, as shown in FIG. 1.

In an embodiment of the invention, the invention provides a membrane-less reactor based on design of GDE to increase $CO_2$ solubility and its conversion via single pot microbial electrosynthesis. In another embodiment, the working electrode is a GDE, wherein the active layer is modified with electro-active material to increase the reaction rates. In another embodiment, the electrode arrangement is in such a way that the oxygen generated at counter electrode is washed away without contacting the working electrode, as both the counter electrode and working electrode are perpendicular to each other.

In another embodiment, a bio-electroactive filter is present in association with the active layer of GDE that will host the potential electroactive biofilm for efficient $CO_2$ transformation into alcohols. This enables higher microbial growth and faster reaction rates. In another embodiment, the two stage conversion of $CO_2$ to alcohols via organic acids is carried out in single pot using the GDE and bio-electroactive filter arrangement. This invention is based on membrane-less reactor design for faster and efficient $CO_2$ transformation to alcohols.

In one feature, the reactor is single chambered and can be operated in batch or continuous or semi-continuous mode in continuous stirred tank reactor (CSTR) or in sequential batch reactor (SBR).

In yet another feature, the working electrode of the reactor is GDE for $CO_2$ reduction reaction. The active layer of GDE is made of activated carbon powder combined with graphite in 60:40 proportions. The disclosed GDEs are unique in design and fabrication. While the gas supply can be improved by changing the porosity of the gas diffusion layer (GDL), which in standard VITO electrode is 70%. In the new design, this will be further increased to allow more $CO_2$ by increasing the amount of pore former in the GDL. Yet another innovative feature is the variable thickness of the overall electrode which was obtained by varying the thickness of the carbon catalyst layer as well the GDL. This modification of the electrode thickness allows better control on the amount of gas that reaches the biocatalyst in the microbial electrosynthesis system. Finally, besides the conventional flat planar nature of these electrodes, a tubular shaped electrode with possibility of having the gas compartment either towards the inner core (the GDL on the inside) or towards the outside (electrolyte in the inner core) does open up unique design and operational possibilities for MES systems.

In an embodiment, the modification of active layer can be done using different electrocatalytically active materials viz., CNT, graphene, charcoal, metal oxides of nickel, or zinc, or iron, etc. The loading of material should be in the range of 0.4-0.6 mg/cm$^2$ of electrode surface area. These additional electrocatalytically active materials allow improvement in the electrochemical hydrogen production at lower applied overpotentials in the MES system which is considered as the limiting factor in the up scaling of MESs.

In another embodiment, the working electrode is further modified by polymerizing the redox mediators like neutral red, methylene blue, EDTA, phenazine derivatives, etc. Polymerization of the selected material on the electrode should be carried out electrochemically by dissolving it in electrolyte at a concentration of 0.4-0.6 mM.

In one feature, the counter electrode is highly active in nature and made up of titanium or nickel or mixed metal oxide (ruthenium or iridium) coated titanium. Further, the electrode should be coated with highly active materials like, fluidized activated carbon particles, carbon nano-fiber mat, composite of PPy/anthraquinone-2,6-disulfonic disodium salt, compositor of MWCNTs and $SnO_2$, composite of polyaniline/mesoporous tungsten trioxide, or a combination thereof. The concentration should be in the range of 0.6-0.8 mg/cm$^2$.

In yet another feature, the working electrode is preferably cylindrical, arranged vertically inside the reactor in such a way that the $CO_2$ can be passed into the inner side of the cylinder and allowed to diffuse into the electrolyte.

The counter electrode is preferably circular disc shaped with mesh kind of arrangement having wider holes and central cavity.

The arrangement of working and counter electrodes should be perpendicular to each other to avoid the oxygen contact at working electrode. The placement of the counter electrode should be on top of the electrolyte, while the working electrode is completely immersed in the electrolyte with the active layer facing towards electrolyte and gas diffusion layer towards inner side of cylinder without contacting the electrolyte.

In another embodiment, the energy required for carrying out the reaction can be supplied from any renewable source like solar or wind or geo-thermal or grid etc.

The feedstock for the reactor can be $CO_2$ alone or flue gas from any industry having minimum 14% $CO_2$ along with other pollutant gases, viz., SOx, NOx, CO and $H_2S$. The flow rate of gas should be maintained in such a way that the reactor pressure should be maintained at a range of 2-10 bar. Even though the VITO CORE® electrodes are mechanically very strong and capable of handling some overpressure, in this case, they will be further strengthened by increasing the thickness of either the working catalyst layer or the gas diffusion layer or both. This will be achieved making thicker cakes at the beginning and then by controlled calendaring of the cakes up to the desired thickness.

In yet another embodiment, the microbes used in the present invention may include electro-active bacteria (EAB), chemoautotrophic bacteria, heterotrophic bacteria, homoacetogenic bacteria and which can work in synergistic interaction with each other. Bacteria that can be used in the present inventions preferentially include but not limited to *Enterobacter aerogenes* MTCC 25016, *Alicaligens* sp. MTCC 25022, *Geobacter anodireducens*, *Schewanella abyssi*, *S. oneidensis*, *S. piezotolerans*, *S. putrefaciens*, *Shewanella* sp. MTCC 25020, *Pseudomonas aeruginosa*, *Pseudomonas fragi* MTCC 25025, *P. alcaligenes*, *P. pseudoalcaligenes*, *Serratia* sp. MTCC 25017. The selected bacteria should be grown under electric circuit of about 3 V cell potential for 5-7 days prior to inoculation.

In an embodiment of an invention, following bacteria can also be used to perform the the invention, *P. stutzeri*, *Sporomusa ovate*, *Clostridium ljungdahlii*, *Sporomusa acidovorans*, cyanobacterium *Synechocystis*, *M. cerevisiae*, *Clostridium acetobutylicum*, *Clostridium butyricum*, *Clostridium beijerinckii*, *Clostridium aciditolerans*, *Clostridium carboxidivorans*, *D. thermophilus*, *Propionibacterium acidipropionici*, *Propionibacterium jensenii*, *Propionibacterium lymphophilum*, *Propionibacterium microaerophilu*, *Propionibacterium olivae*, *Propionibacterium propionicus*, *Acetobacterium woodii*, *Sporomusa acidovorans*, cvanobacterium *Synechocystis*, *Pelotomaculum thermopropionicum*, etc.

In one feature, the electrolyte used for the experiment should be composed of trace metal solution (g/L, $NaCl_2$, 10; $NH_4CL$, 1; $K_2HPO_4$, 0.3; $KH_2PO_4$, 0.3; $MgCl_2$, 0.2; $CaCl_2$).$2H_2O$, 0.1; KCl, 0.1; $MnO_4.7H_2O$, 0.01; $ZnSO_4.7H_2O$, 0.05; $H_3BO_3$, 0.01; $N(CH_2COOH)$, 4.5; $CaCl_2.2H_2O$, 0.01; $Na_2MoO_4$, 0.01; $CoCl_2.6H_2O$, 0.2; $ALK(SO_4)_2.12H2O$ 0.01; $MgCl_2.6H_2O$, 00.2; $FeCl_3$, 0.1; $CuCl_2.6H_2O$, 0.05) along with $CO_2$ as carbon source.

The reactor can be operated under the applied potential in the range of 1-4 V or applied current anywhere in the range of 50-200 $A/m^2$ with Ag/AgCl reference electrode.

The bio-electro-active filter arranged in association with active layer of GDE should be porous in nature resembling biofilter for higher microbial growth as well as faster reaction rates.

It may include copper coated melamine foam, graphite/carbon felt, graphite/carbon foam, stainless steel felt, stainless steel foam, carbon brush, Porous $Ti_4O_7$ foam, or a combination thereof. In one embodiment, filter material is used on top of which the biofilm may develop.

Figure 2:
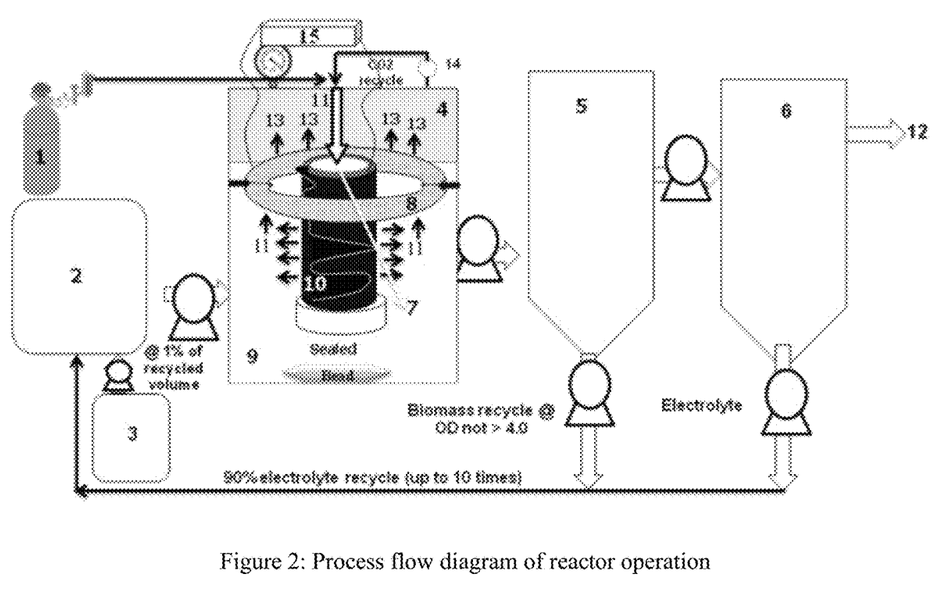
FIG. 2: Process flow diagram of reactor operation.

In yet another embodiment of the invention, a system for production of alcohol from carbon dioxide comprises a carbon dioxide supply or flue gas supply reservoir (1); an electrolyte supply reservoir (2); a trace metal solution (TMS) for providing essential nutrients to microbial metabolism (3); a membrane-less reactor for conversion of carbon dioxide to alcohols (4); a microbial separation column (5); and a product separation column (6). The membrane-less reactor comprises the tubular gas diffusion electrode (7), the circular counter electrode (8), the electrolyte (9) and the porous bio-electroactive filter (10). Further, the carbon dioxide supply reservoir (1) and the electrolyte supply reservoir (2) are connected to the membrane-less reactor (4) for supply of carbon dioxide (11) and electrolyte (9), respectively and the return from microbial separation column (5) and the product separation column (6) are sequentially connected to the membrane-less reactor (4) through the electrolyte supply reservoir (2). The excess $CO_2$ along with the negligible quantities of $O_2$ (13) generated from counter electrode will be recycled to reactor after removing the $O_2$ through $O_2$ scavenging trap on reactor.

FIG. 2 shows the process flow diagram of the reactor operation. A method for production of alcohol (12) using carbon dioxide (1), the method comprising steps of: a) supplying a feed of carbon dioxide and electrolyte to a membrane-less reactor (4); b) carbon dioxide is converted to alcohols in the membrane-less reactor; c) output from the membrane-less reactor passes through the microbe separation column to separate the used microbe from the product stream; and d) this product stream passes through the product separation column to obtain alcohol. In this, the electrolyte is recycled from the product separation column back to the electrolyte reservoir.

In another embodiment of the invention, the feed comprises carbon dioxide having 14% $CO_2$ along with other pollutant gases. The $CO_2$ feed is introduced into the reactor by sparging continuously through flow meter. The membrane-less reactor is operated at a temperature in the range of 25-32° C., pressure in the range of 1-10 bar and at a potential difference of 2-4 V. The method uses biocatalyst selected from a group consisting of electro-active bacteria (EAB), chemoautotrophic bacteria, heterotrophic bacteria, homo acetogenic bacteria and others.

EXAMPLES

Having described the basic aspects of the present invention, the following non-limiting examples illustrate specific embodiments thereof. Those skilled in the art will appreciate that many modifications may be made in the invention without changing the essence of invention.

Example-1 Reactor Design and Operation

Single chambered custom made glass reactor (total/working volume, 0.88/1 L) was used for the experiment. GDE having active layer of activated carbon and graphite powder in 60:40 ratio was used as working electrode. The active layer is initially coated with MWCNT at 0.4 $g/cm^2$ using NAFIONTM binder. Further the electrode was polymerized with neutral red through cyclic voltammogram in half cell reaction. For this purpose, 0.4 mm neutral red solution was prepared in 10 Mm phosphate-buffered saline (PBS) (pH 7.4) and was taken as electrolyte in the WE chamber. Electropolymerization was done by using cyclic voltammetry between −0.8 and +0.8 V at a scan rate of 50 mV/s for about 50 cycles. The electropolymerized electrodes were used for experiment. Titanium mesh coated with composite of PPy/anthraquinone-2,6-disulfonic disodium salt was used as counter electrode in the experiment. Stainless steel wires were used as current collectors for both the electrodes. Stainless steel foam was used for bio-electro-active filter. Leak proof sealing was employed to maintain anaerobic microenvironment. Provision was made in the design for sampling ports. Reactor operation was carried out in CSTR mode in continuous operation and the output was monitored in terms of current consumption in chronoamperometry (CA) and product formation. CO2 sparging was done continuously through flow meter reactor pressure maintained at 2 bar. Experiment carried out at ambient temperature (29±2° C.). The reactor was applied with 3 V of total cell potential using potentiostat-galvanostat system.

Biocatalyst

Four microbial cultures, viz., *Enterobacter aerogenes* MTCC 25016, *Serratia* sp. MTCC 25017, *Shewanella* sp. MTCC 25020, *Pseudomonas fragi* MTCC 25025, were grown separately at 30° C. in a media containing trace metal solution ($NH_4Cl$—0.5 g/l, $MgSO_4$—0.3 g/l, $CoCl_2$—25 mg/l, $ZnSO_4$—11.5 mg/l, $CuSO_4$—10.5 mg/l, $CaSO_4$—5 mg/l, $MnSO_4$—15 mg/i; $NiSO_4$—16 mg/l; $FeSO_4$—25 mg/l) along with 2.5 g of $NaHCO_3$ and 1 g/l of urea under constant applied potential of 5 V. The active microbial cultures were collected by centrifuge (8000 rpm) and mixed in equal proportion to inoculate into the reactor.

Results

Experiment was carried out in continuous mode and the sample collected was analyzed for organic acids and alcohols production. 10 days after start-up, reactor operation showed current consumption of about 26±1.3 A/m$^2$ continuously indicating the stable performance. The product synthesis, initially showed dominant acetic acid and formic acid synthesis but after 6 days of operation, alcohol synthesis observed. From day 12 on wards of reactor operation, consistent dominant alcohol (ethanol and butanol) production observed as depicted in Table 1.

TABLE 1

Consolidated data of experimental output

| | |
|---|---|
| Current consumption (A/m$^2$) | 26 ± 1.3 |
| Total product (g/l/day) | 3.8 ± 0.98 |
| CO$_2$ (soluble) conversion efficiency | 62 ± 1.4 |
| Organic acids (% yield) | 29 ± 1.8 |
| Alcohols (Ethanol and Butanol) (% Yield) | 71 ± 0.86 |

Example-2 Reactor Design and Operation

Single chambered custom made glass reactor (total/working volume, 0.88/1 L) was used for the experiment. GDE having active layer of activated carbon and graphite powder in 60:40 ratio was used as working electrode. The active layer is initially coated with graphene at 0.5 g/cm$^2$ using NAFIONTM binder. Further the electrode was polymerized with methylene blue through cyclic voltammogram in half cell reaction. For this purpose, 0.6 mm methylene blue solution was prepared in 10 mM phosphate-buffered saline (PBS) (pH 7.4) and was taken as electrolyte in the WE chamber. Electropolymerization was done by using cyclic voltammetry between −0.9 and +0.7 V at a scan rate of 40 mV/s for about 50 cycles. The electropolymerized electrodes were used for experiment. Titanium mesh coated with composite of MWCNTs and $SnO_2$ was used as counter electrode in the experiment. Stainless steel wires were used as current collectors for both the electrodes. Porous $Ti_4O_7$ foam was used for bio-electro-active filter. Leak proof sealing was employed to maintain anaerobic microenvironment. Provision was made in the design for sampling ports. Reactor operation was carried out in CSTR mode in continuous operation and the output was monitored in terms of current consumption in chronoamperometry (CA) and product formation. CO$_2$ sparging was done continuously through flow meter reactor pressure maintained at 2 bar. Experiment was carried out at ambient temperature (29±2° C.). The reactor was applied with 3 V of total cell potential using potentiostat-galvanostat system.

Biocatalyst

Four microbial cultures, viz., *Enterobacter aerogenes* MTCC 25016, *Serratia* sp. MTCC 25017, *Alicaligens* sp. ATCC 25022, *Pseudomonas fragi* MTCC 25025, were grown separately at 30° C. in a media containing trace metal solution ($NH_4Cl$—0.5 g/l, $MgSO_4$—0.3 g/l, $CoCl_2$—25 mg/l, $ZnSO_4$—11.5 mg/l, $CuSO_4$—10.5 mg/l, $CaSO_4$—5 mg/l, $MnSO_4$—15 mg/l; $NiSO_4$—16 mg/l; $FeSO_4$—25 mg/l) along with 2.5 g of $NaHCO_3$ and 1 g/l of urea under constant applied potential of 5 V. The active microbial cultures were collected by centrifuge (8000 rpm) and mixed in equal proportion to inoculate into the reactor.

Results

Experiment was carried out in continuous mode and the sample collected was analyzed for organic acids and alcohols production. 12 days after start-up, reactor operation showed current consumption of about 21±1.9 A/m$^2$ continuously indicating the stable performance. The product synthesis, initially showed dominant acetic acid and formic acid synthesis but after 9 days of operation, alcohol synthesis was observed. From day 15 on wards of reactor operation, consistent dominant alcohol (methanol) production was observed as depicted in Table 2.

TABLE 2

Consolidated data of experimental output

| | |
|---|---|
| Current consumption (A/m$^2$) | 21 ± 1.9 |
| Total product (g/l/day) | 2.6 ± 1.1 |
| CO$_2$ (soluble) conversion efficiency | 64 ± 0.28 |
| Organic acids (% yield) | 34 ± 1.3 |
| Alcohols (Methanol) (% Yield) | 65 ± 2.6 |

Example-3 Reactor Design and Operation

Single chambered custom made glass reactor (total/working volume, 0.88/1 L) was used for the experiment. GDE having active layer of activated carbon and graphite powder in 60:40 ratio was used as working electrode. Different combinations of materials were used for the active layer modification at 0.5 g/cm$^2$ using NAFIONTM binder. Further the electrode was polymerized with various redox mediators. For this purpose, 0.6 mm of designated mediator solution was prepared in 10 mM phosphate-buffered saline (PBS) (pH 7.4) and was taken as electrolyte in the WE chamber. Electropolymerization was done by using cyclic voltammetry between −0.9 and +0.7 V at a scan rate of 40 mV/s for about 50 cycles. The electropolymerized electrodes were used for experiment. Various combinations of counter electrodes were also evaluated in the experiment. Stainless steel wires were used as current collectors for both the electrodes in all experiments. Further, different porous materials were also used as bio-electro-active filters in different combinations of WE and CE. All the experimental combinations evaluated were listed in Table 3. Leak proof sealing was employed to maintain anaerobic microenvironment. Provision was made in the design for sampling ports. Reactor operation was carried out in CSTR mode in continuous operation. All the experiments were evaluated in both potentiostat and galvanostat mode and the output was monitored in terms of voltage/current in chronoamperometry (CA)/chronopotentiometry (CP) along with the product formation. $CO_2$ sparging was done continuously through flow meter reactor pressure maintained at 2 bar. Experiment was carried out at ambient temperature (29±2° C.). Different combinations of voltage and current have been applied using potentiostat-galvanostat system and the same are listed in Table 3.

Biocatalyst

For carrying out different experimental combinations, different microbial combinations were also selected as listed in Table 3. The microbes were grown separately at 30° C. in a media containing trace metal solution ($NH_4Cl$—0.5 g/l, $MgSO_4$—0.3 g/l, $CoCl_2$—25 mg/l, $ZnSO_4$—11.5 mg/l, $CuSO_4$—10.5 mg/l, $CaSO_4$—5 mg/l, $MnSO_4$—15 mg/l; $NiSO_4$—16 mg/l; $FeSO_4$—25 mg/l) along with 2.5 of $NaHCO_3$ and 1 g/l of urea under constant applied potential of V. The active microbial cultures were collected by centrifuge (8000 rpm) and mixed in equal proportion to inoculate into the reactor.

Results

Diverse combinations of electrodes, redox mediators, bio-electroactive filters, counter electrodes and its coatings, microbes, applied voltage/current, were evaluated in continuous mode and the sample collected was analyzed for organic acids and alcohols production. Each of the combination has shown different start-up time notable current consumption between 10-16 days and the amount of consumption also varied accordingly (Table 3). Irrespective of the combination, all the reactors initially produced formic acid, acetic acid as dominant products along with some butyric acid but after 8-10 days of acid production, alcohol synthesis was observed. Between day 14-18, all the reactor operation showed consistent dominant alcohol (ethanol, methanol and butanol) production as depicted in Table 3. Coulombic efficiency has been increased from 84% to 93%.

TABLE 3

Comprehensive experimental design with various combinations and respective experimental output

| GDE Modification | Redox mediator | Bio-electro active filter | Counter electrode | Microbes used | Applied Voltage (V) or Current (mA/m2) | Product rate (g/l/day) | Alcohol (g/m2/day electrode) | CE (%) |
|---|---|---|---|---|---|---|---|---|
| | | | | Potentiostat mode | | | | |
| | | | Ti | Enterobacter aerogenes MTCC 25016, Geobacter anodireducens, Shewanella sp. MTCC 25020, Pseudomonas aeruginosa, Pseudomonas fragi MTCC 25025 | 1 | 2.32 | 9.35 | 84.00 |
| CNT | NR | GF | Ti—FACP | Geobacter anodireducens, Schewanella abyssi, S. oneidensis, S. piezotolerans, S. putrefaciens, P. alcaligenes, P. Pseudoalcaligenes | 2 | 4.38 | 17.65 | 85.40 |
| Graphene | MB | CF | Ti—MWCNT—SnO2 | Geobacter anodireducens, S. oneidensis, S. putrefaciens, Shewanella sp. MTCC 25020, Pseudomonas aeruginosa, Serratia sp. MTCC 25017 | 1.5 | 4.46 | 17.98 | 86.20 |
| Charcoal | NR | SS Foam | Ni—CNFM | Alicaligens sp. MTCC 25022, Geobacter anodireducens, Schewanella abyssi, Pseudomonas fragi MTCC 25025, P. Alcaligenes | 2 | 4.39 | 17.69 | 85.68 |

TABLE 3-continued

Comprehensive experimental design with various combinations and respective experimental output

| GDE Modification | Redox mediator | Bio-electro active filter | Counter electrode | Microbes used | Applied Voltage (V) or Current (mA/m2) | Product rate (g/l/day) | Alcohol (g/m2/day electrode) | CE (%) |
|---|---|---|---|---|---|---|---|---|
| ZnO-nano | EDTA | Ni Foam | Ni—WO3 | Enterobacter aerogenes MTCC 25016, Alicaligens sp. MTCC 25022, S. putrefaciens, Shewanella sp. MTCC 25020, P. pseudoalcaligenes, Serratia sp. MTCC 25017 | 2.5 | 4.58 | 18.46 | 87.32 |
| CNT | EDTA | CF | Ti—WO3 | Alicaligens sp. MTCC 25022, Shewanella sp. MTCC 25020, Pseudomonas aeruginosa, P. alcaligenes, P. Pseudoalcaligenes | 3 | 4.69 | 18.90 | 86.98 |
| CNT-Fe2O3 | NR | GF | Ti—WO3 | Geobacter anodireducens, Schewanella abyssi, S. oneidensis, S. piezotolerans, S. putrefaciens, Shewanella sp. MTCC | 4 | 5.08 | 20.48 | 88.16 |
| Graphene-Fe2O3 | NR | GF | Ti—AQ | Shewanella sp. MTCC 25020, Pseudomonas aeruginosa, Pseudomonas fragi MTCC 25025, P. alcaligenes, P. pseudoalcaligenes, Serratia sp. MTCC 25017 | 3.5 | 5.57 | 22.45 | 88.64 |
| Charcoal-ZnO | NR + MB | GF | Ti—WO3/AQ | Schewanella abyssi, Pseudomonas aeruginosa, Pseudomonas fragi MTCC 25025, P. alcaligenes, P. Pseudoalcaligenes | 1.5 | 6.01 | 24.22 | 90.12 |
| CNT-ZnO/Fe2O3 | NR + MB | CF + GF | Ti—MWCNT/SnO2 | Geobacter anodireducens, Pseudomonas aeruginosa, Pseudomonas fragi MTCC 25025, P. alcaligenes, P. Pseudoalcaligenes | 1.5 | 6.38 | 25.72 | 90.22 |
| Charcoal-ZnO | NR + MB | GF | Ti—RuO2/AQ | Schewanella abyssi, Pseudomonas aeruginosa, Pseudomonas fragi MTCC 25025, P. alcaligenes, P. Pseudoalcaligenes | 1.8 | 6.42 | 25.13 | 94.11 |

TABLE 3-continued

Comprehensive experimental design with various combinations and respective experimental output

| GDE Modification | Redox mediator | Bio-electro active filter | Counter electrode | Microbes used | Applied Voltage (V) or Current (mA/m2) | Product rate (g/l/day) | Alcohol (g/m2/day electrode) | CE (%) |
|---|---|---|---|---|---|---|---|---|
| CNF-ZnO/Fe2O3 | NR + MB | CF + GF | Ti—IrO2/MWCNT | *Geobacter anodireducens, Pseudomonas aeruginosa, Pseudomonas fragi* MTCC 25025, *P. alcaligenes, P. Pseudoalcaligenes* | 2.2 | 6.19 | 24.12 | 93.24 |
| Charcoal-ZnO | NR + MB | GF | Ti—IrO2/SnO2 | *Schewanella abyssi, Pseudomonas aeruginosa, Pseudomonas fragi* MTCC 25025, *P. alcaligenes, P. Pseudoalcaligenes* | 2.0 | 6.16 | 24.16 | 93.18 |
| CNT-ZnO/Fe2O3 | NR + MB | CF + GF | Ti—RuO2/CNFM | *Alicaligens* sp. MTCC 25022, *Shewanella* sp. MTCC 25020, *Pseudomonas aeruginosa, P. alcaligenes, P. Pseudoalcaligenes* | 2.5 | 5.98 | 23.72 | 93.16 |
| Galvanostat mode | | | | | | | | |
| | | | Ti | *Enterobacter aerogenes* MTCC 25016, *Geobacter anodireducens, Shewanella* sp. MTCC 25020, *Pseudomonas aeruginosa, Pseudomonas fragi* MTCC 25025 | 100 | 2.64 | 10.64 | 84.72 |
| CNT | NR | GF | Ti—FACP | *Geobacter anodireducens, Schewanella abyssi, S. oneidensis, S. piezotollerans, S. putrefaciens, P. alcaligenes, P. Pseudoalcaligenes* | 150 | 4.61 | 18.58 | 86.18 |
| Graphene | MB | CF | Ti—MWCNT—SnO2 | *Geobacter anodireducens, S. oneidensis, S. putrefaciens, Shewanella* sp. MTCC 25020, *Pseudomonas aeruginosa, Serratia* sp. MTCC 25017 | 120 | 4.93 | 19.87 | 86.64 |
| Charcoal | NR | SS Foam | Ni—CNFM | *Alicaligens* sp. MTCC 25022, *Geobacter anodireducens, Schewanella abyssi, Pseudomonas fragi* MTCC 25025, *P. Alcaligenes* | 180 | 5.03 | 20.27 | 85.92 |

TABLE 3-continued

Comprehensive experimental design with various combinations and respective experimental output

| GDE Modification | Redox mediator | Bio-electro active filter | Counter electrode | Microbes used | Applied Voltage (V) or Current (mA/m2) | Product rate (g/l/day) | Alcohol (g/m2/day electrode) | CE (%) |
|---|---|---|---|---|---|---|---|---|
| ZnO-nano | EDTA | Ni Foam | Ni—WO3 | Enterobacter aerogenes MTCC 25016, Alicaligens sp. MTCC 25022, S. putrefaciens, Shewanella sp. MTCC 25020, P. pseudoalcaligenes, Serratia sp. MTCC 25017 | 200 | 5.29 | 21.32 | 88.32 |
| CNT | EDTA | CF | Ti—WO3 | Alicaligens sp. MTCC 25022, Shewanella sp. MTCC 25020, Pseudomonas aeruginosa, P. alcaligenes, P. Pseudoalcaligenes | 160 | 5.47 | 22.05 | 87.96 |
| CNT-Fe2O3 | NR | GF | Ti—WO3 | Geobacter anodireducens, Schewanella abyssi, S. oneidensis, S. piezotolerans, S. putrefaciens, Shewanella sp. MTCC | 140 | 5.83 | 23.50 | 89.22 |
| Graphene-Fe2O3 | NR | GF | Ti—AQ | Shewanella sp. MTCC 25020, Pseudomonas aeruginosa, Pseudomonas fragi MTCC 25025, P. alcaligenes, P. pseudoalcaligenes, Serratia sp. MTCC 25017 | 50 | 6.01 | 24.22 | 90.26 |
| Charcoal-ZnO | NR + MB | GF | Ti—WO3/Ppy/AQ | Schewanella abyssi, Pseudomonas aeruginosa, Pseudomonas fragi MTCC 25025, P. alcaligenes, P. Pseudoalcaligenes | 75 | 6.36 | 25.63 | 92.68 |
| CNT-ZnO/Fe2O3 | NR + MB | CF + GF | Ti—MWCNT/SnO2 | Geobacter anodireducens, Pseudomonas aeruginosa, Pseudomonas fragi MTCC 25025, P. alcaligenes, P. Pseudoalcaligenes | 100 | 6.68 | 26.92 | 93.44 |
| Charcoal-ZnO | NR + MB | GF | Ti—RuO2/AQ | Schewanella abyssi, Pseudomonas aeruginosa, Pseudomonas fragi MTCC 25025, P. alcaligenes, P. Pseudoalcaligenes | 180 | 6.58 | 27.13 | 93.18 |

TABLE 3-continued

Comprehensive experimental design with various combinations and respective experimental output

| GDE Modification | Redox mediator | Bio-electro active filter | Counter electrode | Microbes used | Applied Voltage (V) or Current (mA/m2) | Product rate (g/l/day) | Alcohol (g/m2/day electrode) | CE (%) |
|---|---|---|---|---|---|---|---|---|
| CNT-ZnO/Fe2O3 | NR + MB | CF + GF | Ti—IrO2/MWCNT | *Geobacter anodireducens, Pseudomonas aeruginosa, Pseudomonas fragi* MTCC 25025, *P. alcaligenes, P. Pseudoalcaligenes* | 80 | 6.27 | 25.14 | 94.26 |
| Charcoal-ZnO | NR + MB | GF | Ti—IrO2/SnO2 | *Schewanella abyssi, Pseudomonas aeruginosa, Pseudomonas fragi* MTCC 25025, *P. alcaligenes, P. Pseudoalcaligenes* | 120 | 6.66 | 24.37 | 92.13 |
| CNT-ZnO/Fe2O3 | NR + MB | CF + GF | Ti—RuO2/CNFM | *Alicaligens* sp. MTCC 25022, *Shewanella* sp. MTCC 25020, *Pseudomonas aeruginosa, P. alcaligenes, P. Pseudoalcaligenes* | 100 | 5.98 | 25.78 | 94.31 |

Example-4 Reactor Design and Operation

Single chambered custom made glass reactor (total/working volume, 0.88/1 L) was used for the experiment. GDE having active layer of activated carbon and graphite powder in 60:40 ratio was used as working electrode. To study the impact of flue gas (14% CO2, 500 ppm SOx, 500 ppm NOx and balance nitrogen) as feedstock against pure $CO_2$ (99.99%) was studied under different experimental combinations and electrical modes. Different combinations of electrode modifications, redox mediators, counter electrodes and bio-electro-active filters were used as combinations of WE and CE. All the experimental combinations evaluated were listed in Table 4. Leak proof sealing was employed to maintain anaerobic microenvironment. Provision was made in the design for sampling ports. Reactor operation was carried out in CSTR mode in continuous operation. The same experimental combinations were evaluated in both potentiostat and galvanostat mode along with changing the microbial blend and the output was monitored in terms of voltage/current in chronoamperometry (CA)/chronopotentiometry (CP) along with the product formation. $CO_2$ sparging was done continuously through flow meter reactor pressure maintained at 2 bar. Experiment was carried out at ambient temperature (29±2° C.). Different combinations of voltage and current have been applied using potentiostat-galvanostat system and the same are listed in Table 4.

Biocatalyst

Two sets of microbial blends were used viz., *Geobacter anodireducens, Schewanella abyssi, S. oneidensis, S. piezotolerans, S. putrefaciens, P. alcaligenes, P. Pseudoalcaligenes* for potentiostat mode and *Shewanella* sp. MTCC 25020, *Pseudomonas aeruginosa, Pseudomonas fragi* MTCC 25025, *P. alcaligenes, P. pseudoalcaligenes, Serratia* sp. MTCC 25017 for galvanostat mode operations. The microbes were grown separately at 30° C. in a media containing trace metal solution ($NH_4Cl$—0.5 g/l, $MgSO_4$—0.3 g/l, $CoCl_2$—25 mg/l, $ZnSO_4$—11.5 mg/l, $CuSO_4$—10.5 mg/l, $CaSO_4$—5 mg/l, $MnSO_4$—15 mg/l; $NiSO_4$—16 mg/l; $FeSO_4$—25 mg/l) along with 2.5 g of $NaHCO_3$ and 1 g/l of urea under constant applied potential of 5V. The active microbial cultures were collected by centrifuge (8000 rpm) and mixed in equal proportion to inoculate into the reactor as per designated combinations.

Results

Diverse combinations of electrodes, redox mediators, bio-electroactive filters, counter electrodes and its coatings were used for experimentation with flue gas and $CO_2$ under both potentiostat and galvanostat modes. Microbes were kept constant for potentiostat mode and galvanostat mode. applied voltage/current, were evaluated in continuous mode and the sample collected was analyzed for organic acids and alcohols production. Irrespective of the combinations used, the experiments carried out with flue gas has shown faster start up time of current consumption than the experiments with pure $CO_2$ (Table 4). The product synthesis was also higher in case of experiments with flue gas due to the positive impact of SOx and NOX as electron carriers. Coulombic efficiency has increased to 94% even with the flue gas.

TABLE 4

Comprehensive experimental design with various combinations for evaluating the impact of flue gas against pure CO2 and respective experimental output

| GDE Modification | Redox mediator | Bio-electro active filter | Counter electrode | Applied Voltage (V) or Current (mA/m2) | Feedstock | Product rate (g/l/day) | Alcohol (g/m2/Day electrode) | CE (%) |
|---|---|---|---|---|---|---|---|---|
| Potentiostat mode ||||||||| 
| CNT | | | Ti | 1 | CO2 | 2.19 | 8.83 | 84.36 |
| Graphene | EDTA | CF | Ti—FACP | 3 | CO2 | 4.86 | 19.59 | 88.08 |
| CNT-Fe2O3 | MB | GF | Ti—WO3 | 2.5 | CO2 | 5.33 | 21.48 | 88.52 |
| Charcoal-ZnO | NR + MB | CF + GF | Ti—WO3/AQ | 1.5 | CO2 | 5.84 | 23.54 | 90.26 |
| CNT-ZnO/Fe2O3 | NR + MB | CF + GF | Ti—MWCNT/SnO2 | 2 | CO2 | 6.13 | 24.71 | 90.67 |
| CNT | | | Ti | 1 | Flue gas | 2.45 | 9.88 | 84.67 |
| Graphene-ZnO/Fe2O3 | EDTA | CF | Ti—FACP | 3 | Flue gas | 5.63 | 22.69 | 88.98 |
| CNT-Fe2O3 | MB | GF | Ti—WO3 | 2.5 | Flue gas | 6.17 | 24.87 | 91.04 |
| Charcoal-ZnO | NR + MB | CF + GF | Ti—WO3/Ppy/AQ | 1.5 | Flue gas | 6.97 | 28.09 | 92.77 |
| CNT-ZnO/Fe2O3 | NR + MB | CF + GF | Ti—MWCNT/SnO2 | 2 | Flue gas | 7.02 | 28.30 | 93.68 |
| Galvanostat mode ||||||||| 
| CNT | | | Ti | 100 | CO2 | 2.27 | 9.15 | 83.92 |
| Graphene | EDTA | CF | Ti—FACP | 160 | CO2 | 5.02 | 20.23 | 89.13 |
| CNT-Fe2O3 | MB | GF | Ti—WO3 | 140 | CO2 | 5.47 | 22.05 | 89.47 |
| Charcoal-ZnO | NR + MB | CF + GF | Ti—WO3/AQ | 80 | CO2 | 5.91 | 23.82 | 90.96 |
| CNT-ZnO/Fe2O3 | NR + MB | CF + GF | Ti—MWCNT/SnO2 | 60 | CO2 | 6.32 | 25.47 | 91.09 |
| CNT | | | Ti | 100 | Flue gas | 2.53 | 10.20 | 84.11 |
| Graphene-ZnO/Fe2O3 | EDTA | CF | Ti—FACP | 160 | Flue gas | 5.96 | 24.02 | 89.66 |
| CNT-Fe2O3 | MB | GF | Ti—WO3 | 140 | Flue gas | 6.37 | 25.68 | 90.85 |
| Charcoal-ZnO | NR + MB | CF + GF | Ti—WO3/AQ | 80 | Flue gas | 7.06 | 28.46 | 92.94 |
| CNT-ZnO/Fe2O3 | NR + MB | CF + GF | Ti—MWCNT/SnO2 | 60 | Flue gas | 7.39 | 29.79 | 93.67 |

TABLE 5 name of abbreviation terms

| Abbreviation Term | Name |
|---|---|
| Ti | Titanium |
| NR | Neutral red |
| GF | Graphite foam |
| FACP | Amino-functionalized cyclopentadienyl ligand |
| MB | Methylene blue |
| CF | Carbon foam |
| MWCNT | Multi-walled carbon nanotube |
| CNFM | Carbon nanofibre matrix |
| WO3 | Tungsten trioxide |
| CNT | carbon nanotube |
| EDTA | Ethylene diamine tetra acetic acid |
| AQ | Anthraquinone |
| RuO2 | Ruthenium oxide |
| PPy | Polypyrrole |

Reference number 1 is a carbon dioxide supply or flue gas supply reservoir, reference number 2 is an electrolyte supply reservoir, reference number 3 is a trace metal solution (TMS) for providing essential nutrients to microbial metabolism, reference number 4 is a membrane-less reactor, reference number 5 is a microbial separation column, reference number 6 is a product separation column, reference number 7 is a tubular gas diffusion electrode, reference number 8 is a circular counter electrode, reference number 9 is an electrolyte, reference number 10 is a porous bio-electroactive filter, reference number 11 is supply of carbon dioxide, reference number 12 is production of alcohol, reference number 13 is negligible quantities of $O_2$, reference number 14 is O2 trap through which carbon dioxide or flue gas recirculated and reference number 15 is potentiostat-galvanostat system for application of desired voltage/current.

We claim:

1. A membrane-less reactor for converting carbon dioxide to alcohols by microbial electrosynthesis, the membrane-less reactor comprising:

a) a tubular gas diffusion electrode comprising an active layer, and a gas diffusion layer, wherein the active layer is modified with an electroactive material, wherein the tubular gas diffusion electrode is configured to work as a working electrode, wherein, the active layer faces towards an outside of the working electrode and the gas diffusion layer faces towards an inner core of the working electrode;

b) a circular counter electrode, wherein the circular counter electrode is a circular disc shaped mesh having a central cavity;

c) a porous bio-electroactive filter, wherein the porous bio-electroactive filter is arranged in association with the active layer of the tubular gas diffusion electrode and is configured to develop an electro-active biofilm, and wherein the electro-active biofilm comprises a biocatalyst for the microbial electrosynthesis;

d) an electrolyte; and e) samplings ports;

wherein the working electrode and the circular counter electrode are positioned perpendicular to each other such that oxygen generated at counter electrode is washed away without contacting the working electrode, and the working electrode is vertically arranged inside the membrane-less reactor such that it remains completely immersed in the electrolyte, wherein the active layer faces towards the electrolyte and gas diffusion layer faces towards the inner core of the working electrode without contacting the electrolyte, thus forming a gas compartment towards the inner core of the working electrode, and wherein the counter electrode is positioned on top of the electrolyte;

wherein the membrane-less reactor is configured to be operated in a batch mode in a sequential batch reactor, or in a continuous or semi-continuous mode in a continuous stirred tank reactor.

2. The membrane-less reactor as claimed in claim 1, wherein the active layer of the working electrode comprises:
   a) an activated carbon powder and graphite in 60:40 proportion; and
   b) the electroactive materials present in a concentration range of 0.4-0.6 mg/cm$^2$.

3. The membrane-less reactor as claimed in claim 1, wherein the working electrode is treated with polymerized redox mediators dissolved in the electrolyte at a concentration of 0.4-0.6 mM;
   wherein the electrolyte comprises trace metal solution along with carbon dioxide as a carbon source.

4. The membrane-less reactor as claimed in claim 1, wherein the counter electrode is made up of titanium, nickel, or titanium coated with mixed metal oxide of ruthenium or iridium, and wherein the counter electrode is coated with a coating of highly active materials with a concentration in range of 0.6-0.8 mg/cm2.

5. The membrane-less reactor as claimed in claim 1, wherein the feedstock for the reactor is $CO_2$ alone or a flue gas having 14% $CO_2$ along with other pollutant gases.

6. The membrane-less reactor as claimed in claim 1, wherein the biocatalyst is a microbe selected from a group consisting of an electro-active bacteria (EAB), a chemoautotrophic bacteria, a heterotrophic bacteria, and a homo acetogenic bacteria, wherein the microbe is grown under 3 V cell potential for 5-7 days prior to inoculation.

7. The membrane-less reactor as claimed in claim 1, wherein the membrane-less reactor is operated at a pressure in a range of 2-10 bar by maintaining a flow rate of the feedstock and a potential in a range of 1-4 V or applied current in a range of 50-200 A/m2.

8. A system for production of alcohol from carbon dioxide, said system comprising:
   a carbon dioxide supply reservoir or a flue gas supply reservoir;
   an electrolyte supply reservoir;
   a trace metal solution (TMS) for providing essential nutrients to microbial metabolism;
   a microbial separation column;
   a product separation column; and
   a membrane-less reactor for conversion of carbon dioxide to alcohols, wherein, the membrane-less reactor comprises a) a tubular gas diffusion electrode comprising an active layer, and a gas diffusion layer, wherein the active layer is modified with an electroactive material, wherein the tubular gas diffusion electrode is configured to work as a working electrode, wherein, the active layer faces towards an outside of the working electrode and the gas diffusion layer faces towards an inner core of the working electrode, b) a circular counter electrode, wherein the circular counter electrode is a circular disc shaped mesh having a central cavity, c) a porous bio-electroactive filter, wherein the porous bio-electroactive filter is arranged in association with the active layer of the tubular gas diffusion electrode and is configured to develop an electro-active biofilm, and wherein the electro-active biofilm comprises a biocatalyst for the microbial electrosynthesis, d) an electrolyte, e) samplings ports,
   wherein the working electrode and the circular counter electrode are positioned perpendicular to each other such that oxygen generated at counter electrode is washed away without contacting the working electrode, and the working electrode is vertically arranged inside the membrane-less reactor such that it remains completely immersed in the electrolyte, wherein the active layer faces towards the electrolyte and gas diffusion layer faces towards the inner core of the working electrode without contacting the electrolyte, thus forming a gas compartment towards the inner core of the working electrode, and wherein the counter electrode is positioned on top of the electrolyte, and wherein the membrane-less reactor is configured to be operated in a batch mode in a sequential batch reactor, or in a continuous or semi-continuous mode in a continuous stirred tank reactor, wherein the carbon dioxide supply reservoir and the electrolyte supply reservoir are connected to the membrane-less reactor and supply carbon dioxide and electrolyte respectively and the microbial separation column and the product separation column are sequentially connected to the membrane-less reactor through the electrolyte supply reservoir.

* * * * *